United States Patent [19]

Rice

[11] 4,368,326
[45] Jan. 11, 1983

[54] SHORT TOTAL SYNTHESIS OF DIHYDROTHEBAINONE, DIHYDROCODEINONE, AND NORDIHYDROCCODEINONE

[76] Inventor: Kenner C. Rice, 14704 Red Fox Rd., Rockville, Md. 20852

[21] Appl. No.: 350,221

[22] Filed: Feb. 19, 1982

Related U.S. Application Data

[63] Continuation-in-part of Ser. No. 165,690, Jul. 3, 1980, abandoned.

[51] Int. Cl.$^3$ ............... C07D 489/02; C07D 221/28; C07D 217/20
[52] U.S. Cl. ..................... 546/45; 546/15; 546/74; 546/146; 546/149
[58] Field of Search ............ 546/44, 45, 46, 74

[56] References Cited

U.S. PATENT DOCUMENTS 3,438,989  4/1969  Shavel, Jr. et al. ............ 546/74
4,003,903  1/1977  Schwartz ..................... 546/44 X

FOREIGN PATENT DOCUMENTS 7107921  12/1971  Netherlands .
1330581  9/1973  United Kingdom .

OTHER PUBLICATIONS

Birch, et al., "Reduction by Metal-Ammonia Solution and Related Reagents," Advances In Organic Chemistry, vol. 8, Wiley-Interscience, 1972, pp. 1–65.
May et al., "Morphine and Its Modifications," Medicinal Chemistry, vol. 5, D. Stephens, Analgesics, 1965, pp. 123–174.
Rice, J. Org. Chem., vol. 45, No. 15, pp. 3135–3137 (07/18/80).
Herlem, Pure & Appl. Chem., vol. 49, pp. 107–113, (1977).
Gesson, et al., Chemical Abstracts, vol. 88, 152297g, (1978).
Grewe, et al., Chem. Ber., 100, 1550–1558, (1967).
Friedrichsen, Chem. Ber., 101, 1190–1194, (1968).
Maeda, et al., Chemical Abstracts, vol. 69, 52367u, (1968).
Sawa, et al., Chemical Abstracts, vol. 73, 131195x, (1970).
Hellerbach, et al., "Synthetic Analgesics," Part IIA, Morphinans, Pergamon Press, 1966, pp. 1–104.
DeGraw, et al., J. Heterocyclic Chem., vol. 11, pp. 363–367, (1974).
Beyerman, et al., Recl. Trav. Chim. Pays-Bas, 95, pp. 184–188, (1976).
Beyerman, et al., Recl. Trav. Chim. Pays-Bas, 97, pp. 127–130, (1978).
Beyerman, et al., Chemical Abstracts, 91, 74760y, (1979).
Gesson, et al., J. Chem. Soc., Chem. Comm., pp. 652–653, (1976).
Fieser, et al., Reagents for Organic Synthesis, vol. 6, John Wiley Sons, New York, 1977, pp. 617–618.

*Primary Examiner*—Donald G. Daus
*Assistant Examiner*—Diana G. Rivers
*Attorney, Agent, or Firm*—John S. Roberts, Jr.

[57] ABSTRACT

A method of producing morphinan compounds which incorporates double advantages over the prior art, such as the utilization of $\beta,\gamma$-unsaturated ketones in place of the $\alpha,\beta$-unsaturated ketones previously used. Additionally, in the step where $\beta,\gamma$-unsaturated bromoketones (13 or 14) proceed to 1-bromo-N-formylnordihydrothebainone (morphinan) (17) there are utilized super acids, such as trifluoromethane sulfonic, trifluoroethane sulfonic and mixtures thereof, and also antimony pentafluoride and mixtures of hydrogen fluoride and antimony pentafluoride. Super acid works, whereas the prior art shows that cyclization in the presence of acids, even strong acids, such as sulfuric, phosphoric, do not work.

1 Claim, No Drawings

SHORT TOTAL SYNTHESIS OF DIHYDROTHEBAINONE, DIHYDROCODEINONE, AND NORDIHYDROCCODEINONE

This application is a continuation-in-part application of Ser. No. 165,690 filed July 3, 1980, now abandoned.

The present application relates to compounds which may be described as morphine agonists and antagonists. The synthesis utilized is capable of producing all of the medically important opium derivatives of the morphinan type, including thebaine.

Among the advantages emphasized by the present invention are the utilization of β, γ-unsaturated ketones where in the past there have been used α,β-unsaturated ketones. Secondly, in the step below where β,γ-unsaturated bromoketones (13 or 14) proceed to 1-bromo-N-formylnordihydrothebainone (morphinan) (17), in this process there are utilized super acids, such as trifluoromethane sulfonic, trifluoroethane sulfonic and mixtures thereof, and also antimony pentafluoride and mixtures of hydrogen fluoride and antimony pentafluoride. An additional advantage of the present process is that oxide bridge closure is accomplished in the N-nor series bromonordihydrothebainone (18)→nordihydrocodeinone (21), thus affording ready access to either N-nor or N-methyl derivatives from the same intermediate 18. N-nor derivatives are of paramount importance in the synthesis of narcotic antagonists and the agonist-antagonist drugs. The N-methyl derivative, dihydrocodeinone (22), is a key intermediate which can be converted by established methods to codeine, morphine, thebaine and all medically valuable opium derivatives of the morphinan type.

In this specification, morphine-type means alkaloid compounds generally of the morphinan structure. Specially interesting are morphine and morphinan agonists and antagonists.

Grewe codeine method is a ring closure method utilizing bromine as a blocking group and deactivating influence on the phenolic ring (cf. *J. Het. Chem.*, June 1974, 363).

Birch reduction includes reduction with ammonia or lower amine and lithium (preferred) or other alkali metal.

The introduction of bromine in a 1:1 ratio followed by alkali metal base served to close the oxide bridge. In a process proceeding from bromonordihydrothebainone (18) the bridge head nitrogen may be alkylated using an acid aldehyde, a lower aldehyde, or ketone such as theyl aldehyde or acetone.

The chart below is a synopsis of the sequence of steps.

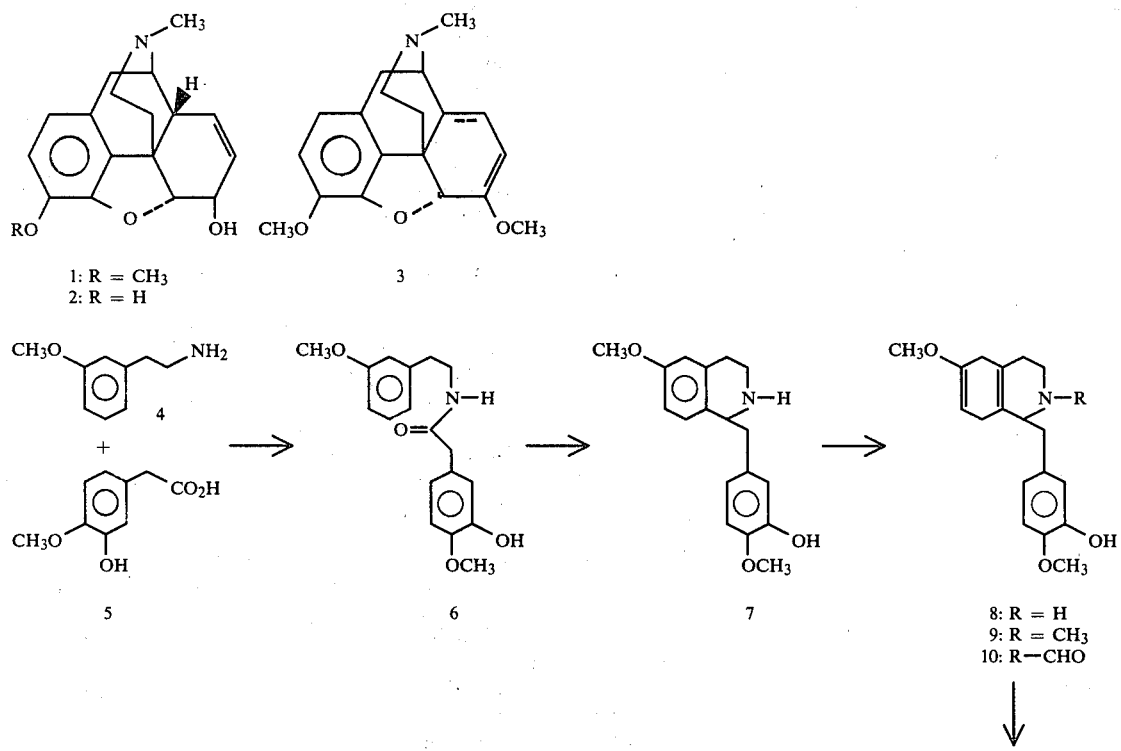

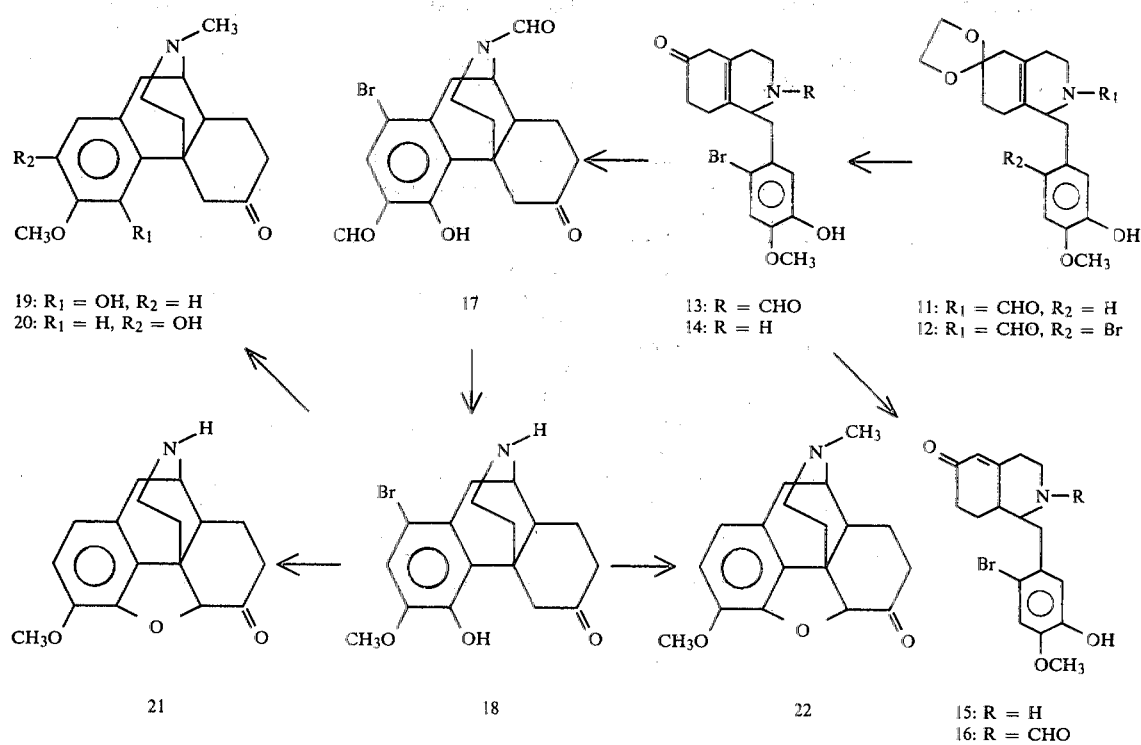

19: R₁ = OH, R₂ = H
20: R₁ = H, R₂ = OH

17

13: R = CHO
14: R = H

11: R₁ = CHO, R₂ = H
12: R₁ = CHO, R₂ = Br

21

18

22

15: R = H
16: R = CHO

Prior Art Statement

British Pat. No. 1,330,581 and Netherlands Pat. No. 7,107,921—Any pertinency of these two patents is diminished by published studies [Beyerman et al, Recl. Trav. Chim. Pays-Bas, 95:184 (1976), and DeGraw et al, J. Heterocyclic Chem., 11:363 (1974)]. These two Merck patents claim Grewe cyclization to N-acyl derivatives of morphinan 18. The present invention shows that only β,γ-unsaturated bromoketone will operate as precursors for the morphinan carbon-nitrogen skeleton.

DeGraw et al, J. Heterocyclic Chem., 11:363 (1974), see page 367, footnote 4.

Beyerman et al, Recl. Trav. Chim., 95:184 (1976), see page 2, column 1.

Birch et al, "Reduction by Metal-Ammonia Solution and Related Reagents," Advances in Organic Chemistry, Vol. 8, Wiley-Interscience, 1972, pages 1–65.

May et al, "Morphine and Its Modifications," Medicinal Chemistry, Vol. 5, D. Stevens, Analgesics, 1965, pages 123–174.

International Series of Monographs in Organic Chemistry, Vol. 8, Synthetic Analgesics, Part 2-A, Morphinans, Pergamon Press, 1966, page 1–104.

Science, Vol. 206, No. 4414, Oct. 5, 1979, pp 13–20.

Rice, J. of Organic Chemistry, Vol. 45(15), July 18, 1980, pp. 3135–3137.

With reference to the use of super acids, the invention encompasses such acids as trifluoromethane sulfonic, trifluoroethane sulfonic, etc., and it is maintained that the use of these very strong acids overcomes the difficulty of use of acids, such as sulfuric, phosphoric, etc.

Relative to the compounds produced by alkylating the nitrogen bridge head, this reaction will work with lower amines and lower ketones. The utility of the products akin to nordihydrocodeinone (21) with N-alkylate are morphine agonists or antagonists. These compounds with the N-alkylate structure are denoted as tertiary amines and specially where N-methyl, N-ethyl, etc., are produced and the alkyl chain is $C_1$-$C_6$. Of the ketones, acetone and methyl ethyl ketone will operate. They are regarded as quite important for morphine overdose.

In general, as to utility, dihydrothebainone (19) is noted in J. Med. Chem., 19:1171 (1976) and dihydrocodeinone (22) is a prescription drug on the market at present produced by Mallinckrodt, etc., as Hydrocodone.

As a general summary of the above chart, the following general description is made commencing with codeine (1).

Racemic dihydrothebainone (19), nordihydrocodeinone (21) and dihydrocodeinone (22) were synthesized in high overall yield from 3-methoxyphenethylamine (4), via the key intermediate (±)-1-bromonordihydrothebainone (18); the route utilized unprotected phenolic intermediates, involved directed Grewe-type cyclization and for 21 and 22, exploited novel oxide bridge closure in the N-nor series.

Natural (−)-codeine (1) continues to occupy a position of central importance among the medically valuable derivatives of the opium poppy as the most frequently prescribed analgesic-antitussive agent worldwide. Since the first total synthesis of (−)-codeine (1) and (−)-morphine (2), other successful routes, including Grewe-type and biomimetic approaches, have appeared. However, a practical total synthesis of these drugs has remained elusive. These and continuing efforts, together with possible shortages, underscore the desirability of securing a route which could render licit production of medical opiates independent of the natural and sole commercial source of these drugs. Since the reports that Grewe-type electrophilic cyclization of (±)-1-benzylhexahydroisoquinoline (9) afforded a 3% yield of the codeine precursor dihydrothebainone (19) (with isomeric 20 as the vastly predominant cyclization product), several groups have attempted to utilize this approach to codeine by introduction of a blocking substituent at the 1-position of the benzyl moiety in order to direct cyclization to the desired dihydrothebainone oxygenation pattern. Studies utilizing a 1-methyl substituent were successful in this regard. However, such an approach must also employ a readily removable group to be of value in synthesis of codeine and congeners, of course, not the case in the 1-methyl series. Substitution of bromine for methyl, unsuccessful hithertofore, would be ideal, since transformation of 4-hydroxymorphinans such as 19 to 22 (with the oxide bridge closed as in codeine) first involves bromination at C-1 of the morphinan system and alter removal of the C-1 bromine atom by hydrogenolysis. Recent work describing conversion of (−)-dihydrothebainone ](−)-19] to (−)-codeine (1) (68% overall), via (−)-dihydrocodeinone, [(−)-22] and to (−)-thebaine (3), (an important minor opium alkaloid) in somewhat higher yield, renders any totally synthetic approach yielding 1-bromodihydrothebainone derivatives still more attractive. Such an approach which utilizes unprotected phenolic intermediates is short, experimentally simple, and affords (±)-dihydrothebainone (19), (±)-nor-dihydrocodeinone (21) and (±)-dihydrocodeinone (22) in high overall yield via the key intermediate (±)-1-bromonordihydrothebainone (18) is included in this disclosure. The sequence rests essentially on high yield preparation of $\beta,\gamma$-unsaturated bromoketone 13, that is converted by directed Grewe-type cyclization into (±)-1-bromo-N-formylnordihydrothebainone (17), and on the novel oxide bridge closure in the N-nor series, which optionally provides ready access to either N-methyl or N-nor derivatives.

Heating a mixture of amine 4 and pure acid 5 at 200° C. for 2 h under argon afforded amide 6 (95%, EtOAc). Cyclization of 6 (0.35 mol scale) with phosphorous oxychloride generated an aqueous solution of the 1,2-dehydro derivative of 7. The conversion of 6 to the 1,2-dehydro derivative of 7 is carried out under ring closure conditions in an organic solvent such as acetonitrile or other lower alkyl nitriles ($C_1$–$C_6$) containing phosphorous oxychloride. A preferred procedure utilizes a molar ratio of phosphorous oxychloride to 6 of greater than 1 and employs refluxing acetonitrile. When the reaction is complete, evaporation of the solvent and excess phosphorous oxychloride and addition of water to the residue gives an aqueous solution of the 1,2-dehydro derivative of 7.

Neutralization to pH 4–5 with concentrated aqueous $NH_3$ and reduction with an equimolar quantity of $NaCNBH_3$ or sodium borohydride in refluxing 45% MeOH (final concentration) for 1.5 h afforded pure (TLC) 7 (86%), mp 199.5°–201.5° C. Birch reduction with lithium or sodium in liquid ammonia of 85 mmol of unpurified 7 with 1.92 g atom of lithium in 450 ml of liquid $NH_3$, 225 mL each of dry THF and t-BuOH at −55° to −65° C. for 4 h, then at −75° C. until no 7 remained by TLC 9 (∼1.5 h) afforded (90%) essentially pure (TLC) 8, mp 179.5°–181.5° C. Refluxing unpurified 8 with 1.5 equivalents of pure PhOCHO or chloral in 10 volumes of EtOAc until homogeneous then ∼0.75 h until TLC showed absence of 8 gave (94%) pure 10, mp 141°–143° C. (Et$_2$O-PhOH) which, as the N-formyl derivatives described below and others, existed as two distinct rotomers, as shown by NMR. This N-formyl derivative introduces a protective group for the nitrogen in the subsequent steps of the reaction. Compound 7 or 8 may be N-methylated with methyl halide or sulfonate to give compound 9. Stirring a solution of 10 (25° C., 1 h) in 20 volumes of dry THF containing 1% (v/v) $CH_3SO_3H$ and 3 molar equivalents of ethylene glycol generated a solution of ketal 11 (quantitatively by TLC) which was treated at 0°–5° C. during 0.5 h with 1.05 equivalents of recrystallized N-bromoacetamide (NBA) to afford essentially pure bromoketal 12 after neutralization with $NH_3$ gas, solvent evaporation and workup with $CHCl_3$-$H_2O$. Bromoketal 12, mp 182.5°–184° C., (EtOAc) could be readily isolated in 88% yield but was most efficiently deketalized in 6 volumes of 5:1 88% $HCO_2H$-$H_2O$ (25° C., 1 h) followed by $CHCl_3$-aqueous $NaHCO_3$ workup to afford 13, mp 203.5°–206.5° C. (DMF-EtOAc), IR ($CHCl_3$) 1717 (C=O) and 1665 (NCHO) cm,$^{-1}$ in 90% yield from 10.

Bromoketone 13 underwent Grewe-type cyclization to (±)-1-bromo-N-formylnordihydrothebainone (17), mp 229.5°–231.5° C. (CMF-$H_2O$) in 60% isolated yield when treated in a screw-capped, high density polyethylene bottle with 14% $NH_4F\cdot HF$ in dry $CF_3SO_3H$ (ammonium fluoride HF complex with trifluoromethane sulfonic acid) (0° C., under argon for 72–96 h until 13 had essentially disappeared by TLC). Also, isomerization of 13 occurred to give (TLC) the $\alpha,\beta$-unsaturated bromoketone 16. Pure 16 afforded (TLC) only traces of morphinan 17 and $\beta,\gamma$-unsaturated ketone 13 under the conditions used to cyclize 13 to 17. Treatment of pure morphinan 17 under these conditions gave no 13 or 16 (TLC); the acid catalyzed equilibrium of 13 and 16 lies nearly exclusively toward the side of the latter, which undergoes little, if any, morphinan cyclization under these conditions. Refluxing isolated 17 in 10:1 MeOH-37% aqueous HCl for 18 h afforded (±)-1-bromonordihydrothebainone (18), mp 220°–223° C. which was easily isolated in 92% yield by workup with $NH_3$-$H_2O$-isopropanol. (±)-Dihydrothebainone (19), mp 173°–175° C., was obtained directly and quantitatively from 17 by hydrolysis as above, evaporation to dryness, and hydrogenation of the residue in 2 N AcOH containing 50 mg 10% Pd/C, 0.3 mL of 37% HCHO and 5 mmol of NaOAc per mmol of 17, followed by workup with $CHCl_3$-aqueous $NH_3$. Bromination (1.1 mol of $Br_2$, 25° C., 2H) of an AcOH solution of the dry residue from hydrolysis of 17, evaporation, treatment of the residue with $CHCl_3$-1 N NaOH and hydrogenation as above without addition of HCHO afforded an 80% yield (from 17) of (±)-nordihydrocodeinone (21), that was readily isolated (isopropanol, 1.1 equivalents of 37% aqueous HCl) as 21.HCl.0.5$H_2O$, mp 292°–295° C. dec; anhydrous 21 base, mp 136.5°–138° C. (PhCH$_3$). This is the first example of closure of the oxide bridge in the basic N-nor series and is of potential interest in the synthesis of narcotic antagonists. When 17 was treated as in the preparation of 21, and 0.3 mL of 37% HCHO/mmol of 17 was added to the hydrogenation medium (±)-dihydrocodeinone (22), mp 158°–160° C., was readily isolated as 22.TsOH, mp 248°–251° C. in 79% yield from 17.

This straightforward total synthesis of (±)-dihydrothebainone (19), (±)-nordihydrocodeinone (21), and (±)-dihydrocodeinone (22) in 37, 30 and 29% overall yields respectively, from readily available 3-methoxyphenethylamine (4) requires isolation of only 6 intermediates. These are directly obtained sufficiently pure for further transformation. In view of these results, the high-yielding conversion of (−)-19 to (−)-thebaine (3) and (−)-codeine (1) discussed above and the facile O-demethylation of the latter to (−)-morphine (2), a practical total synthesis of these alkaloids (and the thebaine based drugs) has resulted.

Resolution of racemic tetrahydroisoquinoline 7 is accomplished by formation and fractional crystallization of diasterisomeric salts with optically active acids such as tartaric, mandelic and tartranilic acid etc. The appropriate optically active base 7 is then regenerated and subjected the reaction sequence described herein to afford morphinan derivatives with the natural morphine absolute configuration.

The term "super acid" or "super acids" is defined to mean and include in this specification and claims the following: All protic acids stronger than 100% sulfuric, thus in this group are perchloric acid $HClO_4$, fluorosulfuric $HSO_3F$, and trifluoromethane sulfonic acid $CF_3SO_3H$, as well as trifluoroethane sulfonic acid. A convenient review incorporating this definition is found in Science, Vol. 26, No. 4414, Oct. 5, 1979, pages 13–20.

I claim:

1. A method which comprises
    (a) heating a mixture of an amine compound of the formula 4

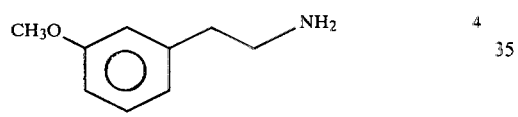

and pure acid compound, formula 5

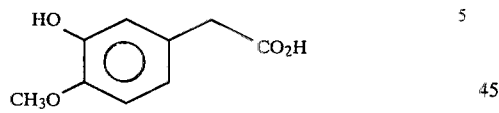

at 200° C. for about 2 hours under argon or other inert gas to obtain amide compound 6 of the following formula

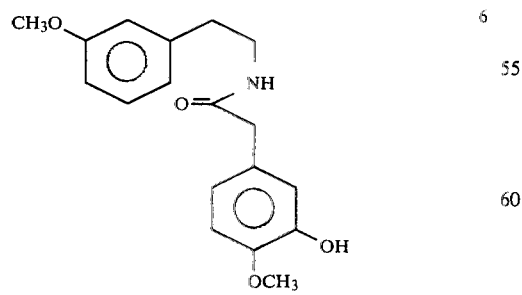

(b) contacting compound 6 with phosphorus oxychloride to produce the 1,2-dehydro derivative of compound 7 shown below:

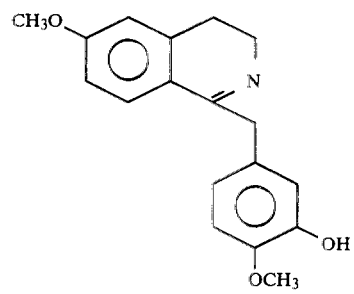

which need not be isolated;

(c) neutralizing the 1,2-dehydro derivative of compound 7 with aqueous ammonia and reducing with sodium cyanoborohydride or sodium borohydride to give the compound tetrahydroisoquinoline 7

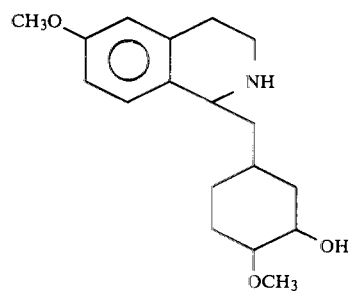

(d) treating of 7 with lithium or sodium in liquid ammonia as a reducing agent to give hexahydroisoquinoline, compound 8

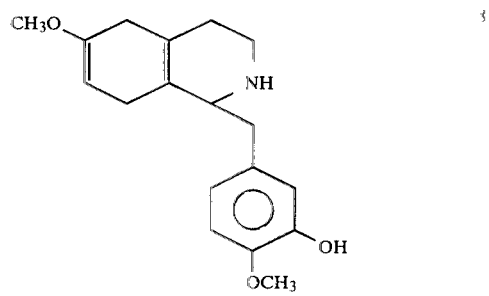

and formylating compound 8 to give 10

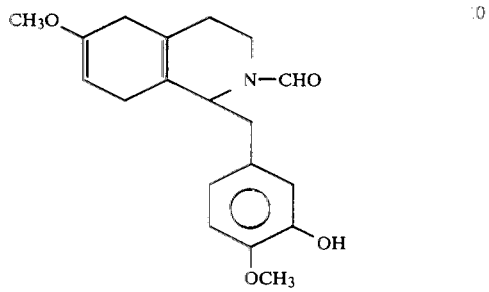

and introducing a protective group for the nitrogen in the subsequent steps of the reaction where the reagent for formylation of 8 to 10 is phenyl formate or chloral;

(e) alternately, N-methylating compound 7 or 8 by treatment with methyl halides or sulfonate to give the N-methyl derivative of 7 or compound 9

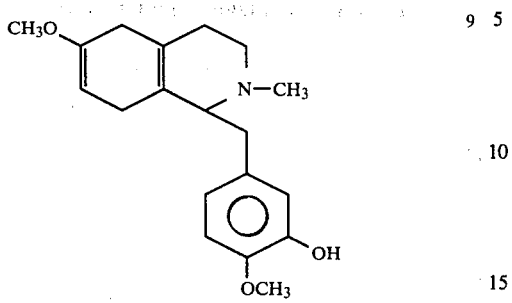

(f) contacting compound 10 with ethylene glycol in dry methane sulfonic acid in dry tetrahydrofuran to afford the ketal product, 11

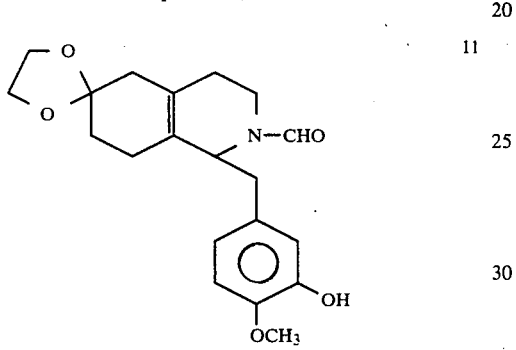

(g) brominating of ketal 11 with N-bromoacetamide (NBA) to give bromo ketal 12

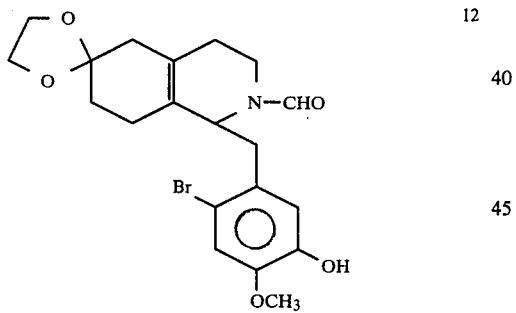

(h) deketalizing bromo ketal 12 with aqueous acid such as aqueous formic acid to yield beta, gamma unsaturated ketone 13

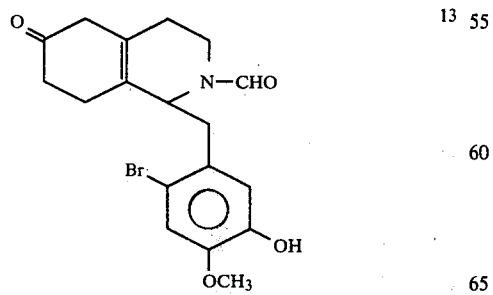

(i) treating beta, gamma unsaturated bromo ketone 13 with a super acid alone or with ammonium fluoride HF complex with trifluoromethanesulfonic acid to give 1-bromo-N-formylnordihydrothebainone 17

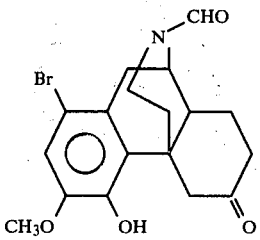

(j) acid hydrolyzing 1-bromo-N-formylnordihydrothebainone 17 with aqueous acid and methanol to give the intermediate 1-bromonordihydrothebainone, compound 18

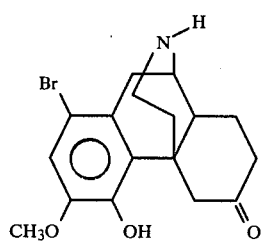

(k) converting intermediate 18, 1-bromonordihydrothebainone, to dihydrothebainone 19, a codeine precursor by hydrogenation in the presence of formaldehyde with palladium on carbon catalyst in 2-normal (2 N) acetic acid containing sodium acetate; or (l) treating intermediate 18 with bromine and acetic acid followed by treating sodium hydroxide to close the oxide bridge and afford as an intermediate 1-bromonordihydrocodeinone which need not be isolated but is hydrogenated in the presence of formaldehyde to give dihydrocodeinone 22, a codeine precursor

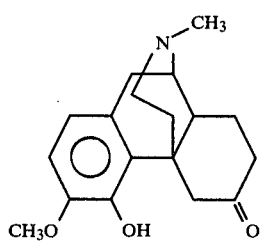

or (m) alternately, converting compound 18 into compound 21, nordihydrocodeinone

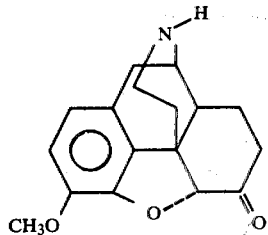
by bromination in acetic acid followed by treating with an aqueous base to close the oxide bridge, and hydrogenating the unisolated intermediate with palladium on carbon catalyst in 2-normal (2 N) acetic acid containing sodium acetate.
* * * * *